(12) United States Patent
Kershaw et al.

(10) Patent No.: US 9,358,251 B2
(45) Date of Patent: Jun. 7, 2016

(54) DISSOLUTION AND PROCESSING OF CELLULOSE

(75) Inventors: David Kershaw, Deeside (GB); Simon Adams, Deeside (GB)

(73) Assignee: CONVATEC TECHNOLOGIES INC., Las Vegas, NV (US)

( * ) Notice: Subject to any disclaimer, the term of this patent is extended or adjusted under 35 U.S.C. 154(b) by 738 days.

(21) Appl. No.: 12/516,001

(22) PCT Filed: Nov. 22, 2007

(86) PCT No.: PCT/GB2007/004488
§ 371 (c)(1),
(2), (4) Date: Jan. 22, 2010

(87) PCT Pub. No.: WO2008/062209
PCT Pub. Date: May 29, 2008

(65) Prior Publication Data
US 2010/0144669 A1 Jun. 10, 2010

(30) Foreign Application Priority Data
Nov. 24, 2006 (GB) .................................. 0623473.6

(51) Int. Cl.
*C08B 11/12* (2006.01)
*C08B 11/20* (2006.01)
*C08B 11/22* (2006.01)
*A61K 31/717* (2006.01)
*A61L 15/28* (2006.01)
*C08J 3/09* (2006.01)
*C08L 1/28* (2006.01)

(52) U.S. Cl.
CPC ............... *A61K 31/717* (2013.01); *A61L 15/28* (2013.01); *C08B 11/12* (2013.01); *C08B 11/20* (2013.01); *C08B 11/22* (2013.01); *C08J 3/096* (2013.01); *C08L 1/286* (2013.01); *C08J 2301/28* (2013.01)

(58) Field of Classification Search
None
See application file for complete search history.

(56) References Cited

U.S. PATENT DOCUMENTS

| 4,246,221 | A |   | 1/1981  | McCorsley, III          |
|-----------|---|---|---------|-------------------------|
| 5,354,790 | A | * | 10/1994 | Keusch et al. ... 523/300 |
| 5,456,745 | A |   | 10/1995 | Roreger et al.          |
| 6,075,177 | A |   | 6/2000  | Bahia                   |
| 2007/0112185 | A1 | * | 5/2007 | Myllymaki et al. ... 536/85 |

FOREIGN PATENT DOCUMENTS

| EP | 0355536 | 2/1990 |
| WO | Wo9312275 | 6/1993 |
| WO | WO03022909 | 3/2003 |
| WO | WO03029329 | 4/2003 |
| WO | WO2007005388 | 1/2007 |
| WO | WO2008043837 | 4/2008 |

OTHER PUBLICATIONS

Heinze et al., cellulose, 1999, 6, 153-165.*
Heinze et al., "Ionic Liquids as Reaction Medium in Cellulose Functionalization" Macromolecular Bioscience (2005) vol. 5 pp. 520-525.*
Paljevac et al., "Ionic Liquids as (Co)Solvents for Enzymatic Reasctions" CI&CEQ (2006) vol. 12 No. 3 pp. 181-186.*

* cited by examiner

*Primary Examiner* — Eric Olson
(74) *Attorney, Agent, or Firm* — Wilson Sonsini Goodrich & Rosati

(57) ABSTRACT

The invention relates to a method for dissolving the components of gel forming materials suitable for use in wound care comprising the steps of admixing said components with an ionic liquid. The ionic liquid may be selected from the group of tertiary amine N-oxides, N,N-dimethyl formamide/nitrogen tetroxide mixtures, dimethyl sulphoxide/paraformaldehyde mixtures and solutions of limium chloride in N,N-dimethyl acetamide or N-methyl pyrrolidone.

13 Claims, No Drawings

DISSOLUTION AND PROCESSING OF CELLULOSE

This invention relates to chemically modified cellulosic materials and particularly chemically modified cellulosic fibres and preferably those which are gel forming materials. Such materials are of particular use in wound care.

Chemically modified cellulose in powder form is well known as a thickener. In particular carboxymethyl cellulose in powder form is produced by the reaction of cellulose pulp with a strong alkali such as sodium hydroxide and monochloroacetic acid or a salt thereof. There have been many suggestions for the production of carboxymethyl cellulose fibres from regenerated cellulose (viscose rayon) fibres or from cotton. There are problems with these methods however in achieving fibres that are suitable for use in wound care because for some applications, highly absorbent fibres which are free of surface stickiness and which are strong enough to be processed on textile machinery are required. Carboxymethyl cellulose fibres suitable for use in wound care have however been produced by the method described in WO 93/12275 which uses solvent spun cellulose fibre as a starting material. This method however has its limitations in that the cellulose has to be chemically converted to the starting material; the carboxymethyl cellulose has to subsequently be converted to a wound care product and the conversion process may not be suitable for all fibre lengths especially short fibres.

The use of ionic liquids to dissolve cellulose is known. WO 03/029329 describes the dissolution and processing of cellulose using ionic liquids Ionic liquids have not however been previously used in the dissolution of gel forming fibres for use in wound care. For instance, for dissolving chemically modified cellulose and particularly water swellable but insoluble carboxymethylcellulose polymers. We have now found that gel forming wound care materials can be produced and modified by using a solvent for the gel forming materials and particularly by dissolving the components that make up the eventual gel forming material in an ionic liquid or other solvent. Surprisingly we have found that when carboxymethyl cellulose polymers are dissolved in an ionic liquid and subsequently regenerated the properties of the modified cellulose are not significantly changed by the process. Accordingly, the invention provides a method for dissolving chemically modified cellulose comprising the steps of admixing chemically modified cellulose with an ionic liquid. By the term ionic liquid is meant a liquid ionic compound which is liquid below 150° C.

The advantage of such a method is that the components of the eventual gel forming material that are admixed with the solvent need not be in a fibrous form. The components could for instance be in the form of a powder prior to dissolution for example a carboxymethylcellulose powder.

Additionally in some embodiments the chemically modified cellulose is rendered into a solution which can be directly processed into any form such as but not limited to fibers, nanofibers, films, coatings, foams, and sponges. These forms are all suitable for use in the treatment of wounds.

In a preferred embodiment the invention provides a solution comprised of a chemically modified cellulose in an ionic liquid solvent wherein said ionic liquid is comprised of a liquid ionic compound which is liquid below 150° C.

In a further preferred embodiment the invention provides a method for regeneration of chemically modified cellulose that comprises admixing a solution of chemically modified cellulose with a liquid non-solvent for the chemically modified cellulose that is miscible with said ionic liquid said admixing causing the cellulose and ionic liquid to form solid and liquid phases.

It has been found that chemically modified cellulose can be dissolved in a number of solvents including tertiary amine N-oxides, N,N-dimethyl formamide/nitrogen tetroxide mixtures, dimethyl sulphoxide/paraformaldehyde mixtures and solutions of lithium chloride in N,N-dimethyl acetamide or N-methyl pyrrolidone and solvents that are described as ionic liquids. The ionic liquid comprises cations and anions in the substantial absence of water, which are molten at a temperature of less than 150° C.

The cations of an ionic liquid are preferably cyclic and correspond in structure to a formula selected from the group consisting of:

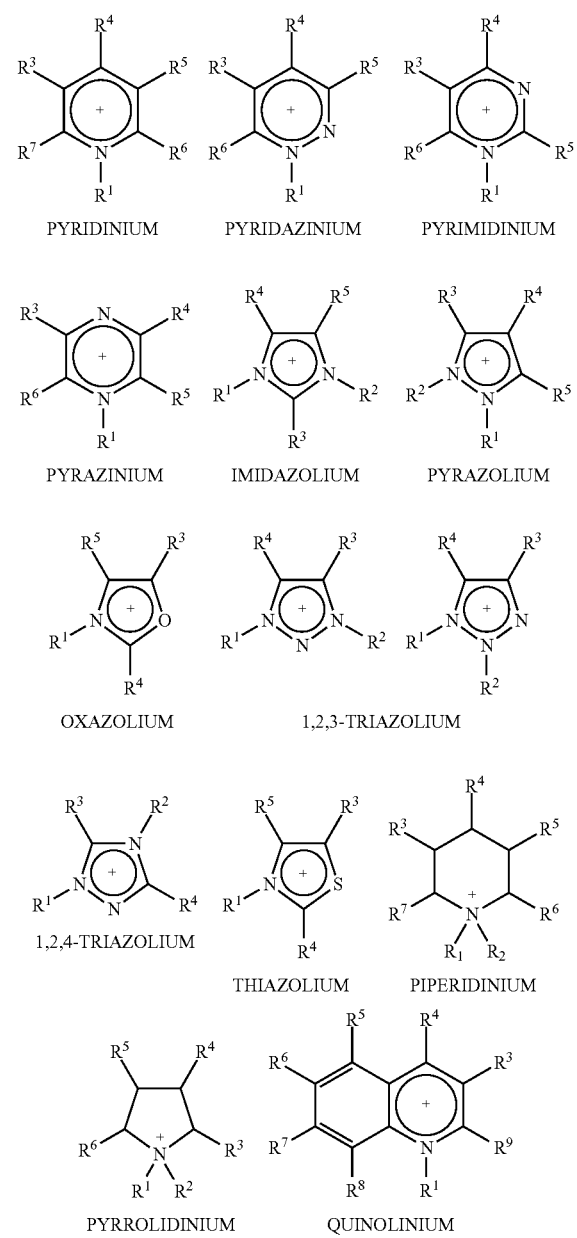

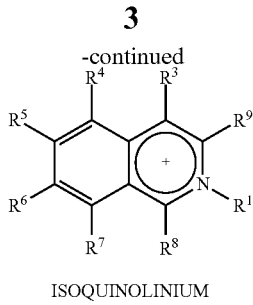

ISOQUINOLINIUM wherein $R^1$ and $R^2$ are independently a $C_1$-$C_6$ alkyl group or a $C_1$-$C_6$ alkoxyalkyl group, and $R^3$, $R^4$, $R^5$, $R^6$, $R^7$, $R^8$ and $R^9$ ($R^3$-$R^9$), when present, are independently a hydrido, a $C_1$-$C_6$ alkyl, a $C_1$-$C_6$ alkoxyalkyl group or a $C_1$-$C_6$ alkoxy group. The anions of the ionic liquid are halogen, pseudohalogen, or $C_1$-$C_6$ carboxylate. It is to be noted that there are two isomeric 1,2,3-triazoles. It is preferred that all R groups not required for cation formation be hydrido.

The anions of an ionic liquid are preferably a halogen ion (chloride, bromide or iodide), perchlorate, a pseudohalogen ion such as thiocyanate and cyanate or C1 to C6 carboxylate. Pseudohalides are monovalent and have properties similar to those of the halides. Pseudohalides include the cyanide, thiocyanate, cyanate, fulminate and azide anions. Carboxylate anions that contain 1 to 6 carbon atoms and are illustrated by formate, acetate, propionate, butyrate, hexanoate, maleate, fumarate, oxalate, lactate, pyruvate and the like.

For the dissolution of modified cellulose we have found that the following ionic liquids are particularly preferred:
butyl-3-methyl imidazolium chloride
1-butyl-1-methylpyrrolidium dicyanamide
N-butyl-4-methylpyridinium dicyanamide By gel forming material is meant hygroscopic material which upon the uptake of exudate become moist and slippery or gelatinous and thus reduce the tendancy of the material to adhere to the wound. The gel forming material can be of the type which retain their structural integrity on absorption of exudate or can be of the type which lose their form and become a structureless gel on absorption of exudate.

The gel forming materials made by the process of the present invention include chemically modified cellulosic fibres and preferably solvent spun sodium carboxymethyl cellulose fibres, and in particular carboxymethylated cellulose fibres as described in PCT WO/9312275. The cellulosic fibres preferably have a degree of substitution of at least 0.05 carboxymethyl groups per glucose unit and a tenacity of at least 10 cN/tex.

The invention will now be described by way of the following examples:

EXAMPLE 1

An ionic liquid, 1-butyl-3-methylimidazolium chloride was placed in a 70 C water bath to melt. Approximately 0.1 gram of degree of fiber as described in patent WO 93/12275 or Aquasorb (manufactured by Hercules Inc) were weighed out into a 20 ml scintillation vial. Sufficient molten ionic liquid was added to the vials to give a final concentration of polymer of 1% by weight. The vials without lids were placed in a microwave oven and heated at maximum power for 5 seconds. The vials were removed and the solution mixed. This was repeated until total dissolution of the polymer was achieved.

The solution was spun by extruding a sample of the solution from a syringe with a 21 guage needle into an excess of IMS, a nonsolvent for the polymer. The coagulated fibres were recovered by filtration.

It was also found that fibres could be electrospun by feeding a sample of the solution through a flat ended 25 guage needle and applying a positive 20 kV charge to the needle. The distance to the ground plate was 15 cm.

A sample of the extruded fibre was hydrated with solution A (sodium/calcium chloride solution BP) and showed similar properties to the starting polymer.

EXAMPLE 2

An ionic liquid, 1-ethyl-3-methylimidazolium acetate was used to make a 2% w/w solution of fiber as described in patent WO 93/12275 and sold under the trademark Aquacel™. The flock of fibres were dispersed in the solvent at ambient temperature but required heating to form a solution.

The solution was spun by extruding a sample of the solution through a Spinneret in the form or either a 400 jet 74 micron diameter parallel sided capillary or the same capillary with a straight sided conical inlet, or the same capillary with a hyperbolically curved inlet cone. The dope velocity was 2 m/min to 10 m/min spun into an excess of ethanol, a non solvent for the polymer. The coagulated fibres were recovered by filtration.

The resulting fibres had a dry fibre average diameter of 15 microns and a hydrated average diameter of 38 microns.

EXAMPLE 3

An ionic liquid, 1-ethyl, 3-methyl imidazolium acetate was used to make a 2% w/w solution of Hercules Aqualon A-500. The powder was dispersed in the solvent at ambient temperature but required heating to form a solution.

The solution was spun by extruding a sample of the solution through a Spinneret in the form or either a 400 jet 74 micron diameter parallel sided capillary or the same capillary with a straight sided conical inlet, or the same capillary with a hyperbolically curved inlet cone. The dope velocity was 2 m/min to 10 m/min and was spun into an excess of ethanol, a non solvent for the polymer. The coagulated fibres were recovered by filtration.

The resulting fibres had a dry fibre average diameter of 29 microns and a hydrated average diameter of 189 microns.

The invention claimed is:

1. A method for dissolving the components of gel forming materials suitable for use in wound care wherein the components comprise carboxymethylcellulose, the method consisting essentially of the steps of admixing said components with an ionic liquid consisting essentially of a liquid ionic compound which is liquid below 150° C., the liquid ionic compound having:

(i) a cation with a structure selected from:

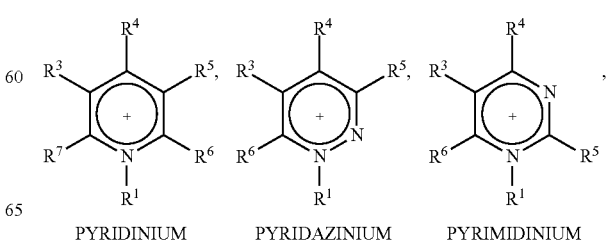

PYRIDINIUM    PYRIDAZINIUM    PYRIMIDINIUM

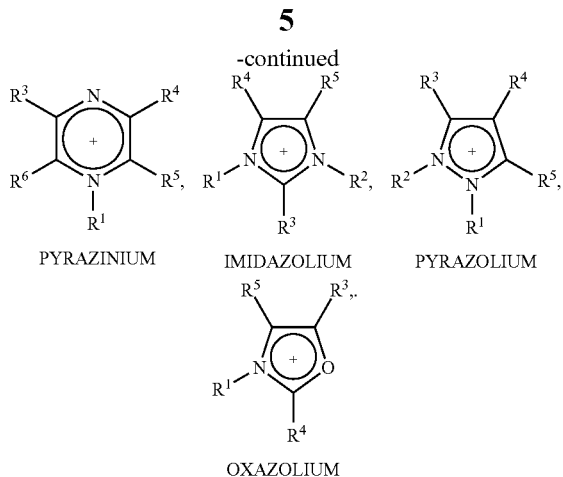

2. The method as claimed in claim 1, wherein the carboxymethylcellulose is a carboxymethylcellulose powder.

3. A method for regeneration of chemically modified cellulose that comprises preparing a solution of chemically modified cellulose, wherein the chemically modified cellulose is a carboxymethylcellulose, in an ionic liquid by dissolving the chemically modified cellulose in said ionic liquid; and admixing the solution with a liquid non-solvent for the chemically modified cellulose that is miscible with said ionic liquid, said admixing causes the cellulose and ionic liquid to form solid and liquid phases, wherein the ionic liquid consists essentially of a liquid ionic compound which is liquid below 150° C. and the properties of the dissolved or regenerated carboxymethylcellulose are similar to the properties of the carboxymethylcellulose prior to dissolution, the liquid ionic compound having:

(i) a cation with a structure selected from:

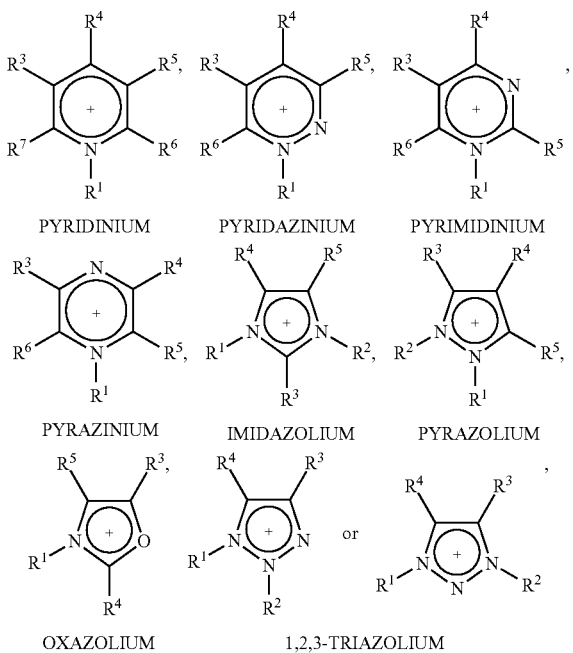

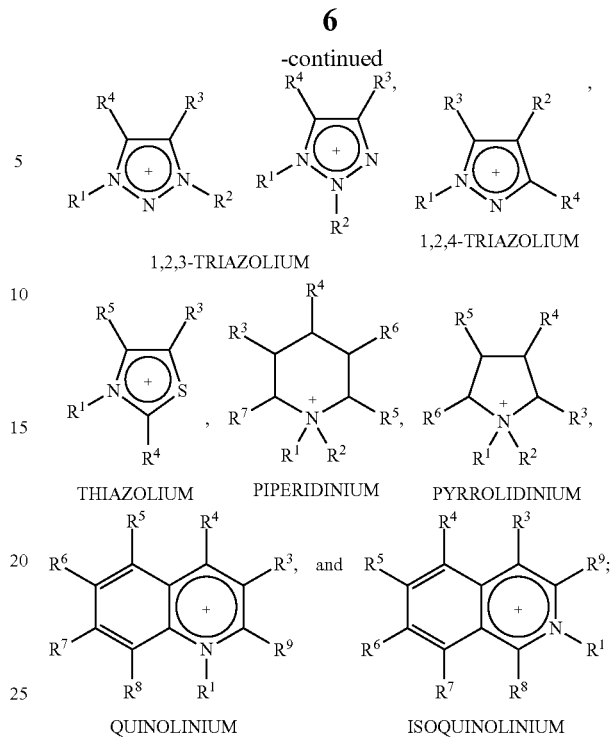

wherein
$R^1$ and $R^2$ are independently $C_1$-$C_6$ alkyl or $C_1$-$C_6$ alkoxyalkyl; and
$R^3$, $R^4$, $R^5$, $R^6$, $R^7$, $R^8$, and $R^9$ are independently H, $C_1$-$C_6$ alkyl, $C_1$-$C_6$ alkoxyalkyl, or $C_1$-$C_6$ alkoxy; and
(ii) an anion selected from halogen, pseudohalogen, or $C_1$-$C_6$ carboxylate.

4. The method as claimed in claim 3, wherein the carboxymethylcellulose is a carboxymethylcellulose powder.

5. The method as claimed in claim 1, wherein the carboxymethylcellulose is processed into a fiber, a nanofiber, a film, a coating, a foam or a sponge.

6. The method as claimed in claim 1, wherein the carboxymethylcellulose is processed into a fiber.

7. The method as claimed in claim 6, wherein the carboxymethylcellulose fiber is sodium carboxymethyl cellulose fiber.

8. The method as claimed in claim 7, wherein the sodium carboxymethyl cellulose fibre has a degree of substitution of at least 0.05 carboxymethyl groups per glucose unit and a tenacity of at least 10 cN/tex.

9. The method as claimed in claim 1, wherein the carboxymethylcellulose is suitable for use in the treatment of wounds.

10. The method as claimed in claim 3, wherein the carboxymethylcellulose is processed into a fiber, a nanofiber, a film, a coating, a foam or a sponge.

11. The method as claimed in claim 3, wherein the carboxymethylcellulose is processed into a fiber.

12. The method as claimed in claim 11, wherein the carboxymethyl cellulose fibre has a degree of substitution of at least 0.05 carboxymethyl groups per glucose unit and a tenacity of at least 10 cN/tex.

13. The method as claimed in claim 3, wherein the carboxymethylcellulose is suitable for use in the treatment of wounds.

* * * * *